(12) United States Patent
Imig et al.

(10) Patent No.: US 6,288,264 B1
(45) Date of Patent: Sep. 11, 2001

(54) PROCESS FOR PREPARING CYANOACETAMIDE

(75) Inventors: Manuela Imig; Manfred Kaufhold, both of Marl; Thomas Kalz, Herne, all of (DE)

(73) Assignee: Degussa-Huels Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/793,420

(22) Filed: Feb. 27, 2001

(30) Foreign Application Priority Data

Mar. 8, 2000 (DE) .............................................. 100 11 191

(51) Int. Cl.[7] ................................................. C07C 255/00
(52) U.S. Cl. .............................................................. 558/445
(58) Field of Search ............................................... 558/445

(56) References Cited

FOREIGN PATENT DOCUMENTS 0 583 694 A1   2/1994   (EP) .

OTHER PUBLICATIONS

H. Gilman, et al. (eds.), Organic Synthesis Collective vol. 1, pp. 178–181, (1972).

*Primary Examiner*—Joseph K. McKane
*Assistant Examiner*—Joseph Murray
(74) *Attorney, Agent, or Firm*—Oblon, Spivak, McClelland, Maier & Neustadt, P.C.

(57) ABSTRACT

Cyanoacetamide is prepared without additional catalyst by esterification of crude cyanoacetic acid with a monohydric alcohol which forms an azeotrope with water and has 4 to 10 carbon atoms, reacting the resulting ester with ammonia in the presence of a basic catalyst to give cyanoacetamide, and work-up by a mechanical separating operation and a thermal treatment.

17 Claims, No Drawings

PROCESS FOR PREPARING CYANOACETAMIDE

BACKGROUND OF THE INVENTION

1. Field of the Invention

The invention relates to a process for preparing cyanoacetamide by esterification without additional catalyst. During this esterification crude cyanoacetic acid is reacted with a monohydric alcohol which forms an azeotrope with water. The resulting ester is reacted with ammonia in the presence of a basic catalyst to give cyanoacetamide, followed by work-up using a mechanical separating operation and thermal treatment.

2. Discussion of the Background

Cyanoacetamide is an important intermediate for preparing drugs and pharmaceutical products. It is used inter alia for preparing malononitrile.

Syntheses of cyanoacetamide from cyanoacetic esters are known from the literature. For example, Organic Synthesis Collect., Volume 1, pg. 179 describes a process in which ethyl cyanoacetate is reacted with concentrated aqueous ammonia. This results in wastewater which is polluted with organic products and which must be disposed of. Moreover, it is necessary to work up the mother liquor to achieve a good yield. Processes of this type are complicated and not economic.

European Patent Application EP-A-0 583 694 describes the use of butanol in a large excess of 5 to 30 times the molar amount of cyanoacetic acid and a strongly acidic catalyst for the esterification. The esterification times are very long despite the catalyst. (For example, a reaction time of 13 hours is disclosed in the Examples of EP-A-0 583 694.

SUMMARY OF THE INVENTION

It is an object of the present invention to develop a process for preparing cyanoacetamide which is technically simple to implement, for example, in an industrial process, with short reaction times and with little complexity. It is another object of the present invention to develop a process for preparing cyanoacetamide, that does not yield waste which is complicated and costly to dispose of.

These and other objects have been achieved according to the invention, the first embodiment of which includes a process for preparing cyanoacetamide from cyanoacetic acid and ammonia, comprising:

(1) optionally, azeotropically distilling out water from cyanoacetic acid with a first monohydric alcohol having 4 to 10 carbon atoms;

(2) esterifying said cyanoacetic acid with a second monohydric alcohol without additional catalyst;
distilling out the water/alcohol mixture, thereby providing a crude ester;

(3) optionally purifying said crude ester by distillation out from high boilers, thereby providing a purified ester;

(4) reacting said crude ester or said purified ester with ammonia in the presence of a basic catalyst, thereby providing crude cyanoacetamide; and (5) working up the crude cyanaoacetamide by a mechanical separating operation and thermal treatment.

DETAILED DESCRIPTION OF THE INVENTION

The object of the present invention is achieved by esterifying a low-cost crude cyanoacetic acid with an unbranched or branched monohydric alcohol having 4 to 10, preferably 4 to 6, carbon atoms without additional catalysts. The resulting ester is further reacted in crude or after only the higher boiling fractions have been removed by distillation. This resulting ester is preferably reacted with gaseous ammonia in the presence of a basic catalyst to give cyanoacetamide.

The work-up takes place by a mechanical separating operation such as filtration or separation in a hydrocyclone, and a thermal treatment such as vacuum-drying.

Surprisingly, it has been found that the synthetic route via the esters, preferably via the butyl esters, provides the following considerable advantages:

the esters can be prepared without an additional catalyst, the work-up of the ester is omitted,
direct conversion to the amide is possible,
with the exception of monohydric alcohol, the mother liquor produced in the amide preparation is free of valuable product, or
additional concentration of the mother liquor can be omitted during repeated crystallization. Thus, the process according to the invention for preparing cyanoacetamide is particularly simple and economic.

The invention therefore relates to a process for preparing cyanoacetamide from crude cyanoacetic acid, which optionally contains water. The process includes the following steps:

(1) Azeotropic distillation with unbranched or branched monohydric alcohols with 4 to 10 carbon atoms to remove the water dissolved in the starting material, where appropriate.

(2) Azeotropic water/alcohol distillation in the esterification of the crude cyanoacetic acid with monohydric alcohols, wherein the esterification is free of additional catalyst.

(3) Optionally, initial purification of the ester by distilling the ester off from high boilers.

(4) Reaction of the ester with ammonia in the presence of a basic catalyst, where appropriate in a monohydric alcohol having 4 to 10 carbon atoms.

(5) Work-up by a mechanical separating operation and a thermal treatment.

The process according to the invention requires no additional solvents either in the first two or in the third stage. It has the advantage that only very small amounts of auxiliaries are required and the monohydric alcohol which is employed in excess can be recovered by simple distillation of high boiling fractions and can be recycled. The preferred monohydric alcohol is butanol.

The molar ratio of alcohol to cyanoacetic acid is 1:1 to 4:1, preferably 1.5:1 to 2.5:1. The molar ratio includes all values and subvalues therebetween, especially including 1.6:1; 1.7:1; 1.8:1; 1.9:1; 2.0:1; 2.1:1; 2.2:1; 2.3:1 and 2.4:1. This ratio determines the bottom temperature under atmospheric pressure, which is preferably not above 140° C. because of the low stability of the acid. For this reason, it is preferable to operate under vacuum conditions. The temperature for the esterification is preferably 100 to 140° C. The temperature includes all values and subvalues therebetween, especially including 105, 110, 115, 120, 125, 130 and 135° C.

Preferred suitable monohydric alcohols are unbranched or branched alcohols which form an azeotrope with water and have 4 to 10, and more preferably 4 to 6 carbon atoms. Butanols are particularly preferred, especially n-butanol and i-butanol.

The catalysts used for reacting the ester with ammonia are compounds which are basic or have a basic action. Preferred catalysts are alkali metal alcoholates or alkaline earth metal alcoholates such as sodium methoxide, potassium methoxide, sodium ethoxide, potassium ethoxide, magnesium methoxide and magnesium ethoxide. These catalysts can be used singly or as mixtures. The catalysts are used in very small amounts of from 0.5 to 10 mol %, preferably 1 to 5 mol % and more preferably 1 to 2.5 mol % of catalyst, based on the amount of acid originally employed.

The ammonia is preferably used in a stoichiometric amount and preferably in the gaseous state. The temperature for reacting the ester with ammonia is 10 to 100° C., preferably 20 to 80° C. The temperature includes all values and subvalues therebetween, especially including 20, 30, 40, 50, 60, 70, 80 and 90° C.

The cyanoacetamide can be purified by recrystallization (see Org. Synthesis Coll. Volume 1, page 179 et seq.). Depending on the required quality, particularly with regard to the color of the cyanoacetamide, it is preferred to prepurify the crude ester before the amide preparation.

The distillation apparatus is preferably a short-path apparatus, and more preferably a short-path evaporator.

Having generally described this invention, a further understanding can be obtained by references to certain specific examples which are provided herein for purposes of illustration only, and are not intended to be limiting unless otherwise specified.

EXAMPLES

Example 1

1.1 Preparation of Butyl Cyanoacetate

A reaction apparatus made of glass with a four-neck flask, stirrer, thermometer, 0.5 m-long distillation column, and distillation apparatus with reflux divider was used. 471.6 g (5.43 mol) of cyanoacetic acid (98% pure) and 886.0 g (11.95 mol) n-butanol were introduced into the flask and heated to 110° C. The butanol/water azeotrope started to distill out at this temperature. After 8.75 hours, 256.7 g of distillate were produced, and the acid number of the bottom product was 11 mg KOH/g, which corresponds to an acid content of only 1.7% by weight.

The reaction product was then worked up by direct distillation, and 695.9 g of butyl ester with a purity of 99.7% were obtained. The yield calculated from this was 90.5% based on the cyanoacetic acid input.

1.2 Preparation of Cyanoacetamide

A glass apparatus consisting of a three-neck flask, stirrer, thermometer and introduction tube was used. 141.6 g (1 mol) of n-butyl cyanoacetate (99.7% pure), 240 g of n-butanol and 3.6 g of sodium methoxide in methanol (30% strength) were mixed and gaseous ammonia was passed in. The exothermic reaction was kept at 30° C. by cooling with water. After 7 hours, GC analysis showed complete conversion of the butyl ester.

The reaction mixture was then filtered, and the filter cake was washed with butanol and dried in vacuum at 40 to 60° C. 76.6 g of cyanoacetamide with a melting point of 120.5–121.5° C. were obtained. The yield was 91% based on the butyl cyanoacetate input. The mother liquor contained no valuable products apart from butanol.

Example 2

The apparatuses described in Example 1 were used. 608 g of 70% pure crude cyanoacetic acid (5.0 mol) which contained 30% water, and 968 g (13.1 mol) of n-butanol were mixed and water was removed. After 8.75 hours, the acid number was 3.0 mg KOH/g, which means that the conversion of acid was more than 99%. 623.3 g of distillate and 953 g of bottom product were obtained. 373.6 g (1.96 mol) of this were diluted with 100 g of n-butanol, and 7.2 g of sodium methoxide solution (30% strength) were added. Then gaseous ammonia was passed in, and the temperature was kept at 30° C. by cooling. The reaction was complete after 7 hours. The work-up as in Example 1 afforded 140.5 g of cyanoacetamide with a melting point of 119.5–121.5° C. The yield over two reaction stages was 85.3% based on crude acid.

The priority document of the present application, German Patent Application No. 100 11 191.2, filed Mar. 8, 2000, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A process for preparing cyanoacetamide from cyanoacetic acid and ammonia, comprising:
    (1) optionally, azeotropically distilling out water from cyanoacetic acid with a first monohydric alcohol having 4 to 10 carbon atoms;
    (2) esterifying said cyanoacetic acid with a second monohydric alcohol without additional catalyst;
    distilling out the water/alcohol mixture, thereby providing a crude ester;
    (3) optionally purifying said crude ester by distillation out from high boilers, thereby providing a purified ester;
    (4) reacting said crude ester or said purified ester with ammonia in the presence of a basic catalyst, thereby providing crude cyanoacetamide; and
    (5) working up the crude cyanaoacetamide by a mechanical separating operation and thermal treatment.

2. The process according to claim 1, wherein said first alcohol is n-butanol or I-butanol.

3. The process according to claim 1, wherein said second monohydric alcohol n-butanol or i-butanol.

4. The process according to claim 1, wherein the molar ratio of said second monohydric alcohol to cyanoacetic acid in the esterification is from 1:1 to 4:1.

5. The process according to claim 1, wherein the molar ratio of said second monohydric alcohol to said cyanoacetic acid is from 1.5:1 to 2.5:1.

6. The process according to claim 1, wherein said purifying of said crude ester proceeds in a short-path distillation apparatus.

7. The process according to claim 6, wherein said short-path distillation apparatus is a short-path evaporator.

8. The process according to claim 1, wherein said basic catalyst is an alkaline metal alcoholate or alkaline earth metal alcoholate.

9. The process according to claim 8, wherein said alkali metal alcoholate is sodium methoxide, potassium methoxide, sodium ethoxide, potassium ethoxide or mixtures thereof.

10. The process according to claim 8, wherein said alkaline earth metal alcoholate is magnesium methoxide, magnesium ethoxide or mixtures thereof.

11. The process according to claim 1, wherein said mechanical separating operation is a filtration or a deposition using a hydrocyclone.

12. The process according to claim 1, wherein said esterifying proceeds at a temperature of from 100 to 140° C.

13. The process according to claim 1, wherein an amount of said basic catalyst is of from 0.5 to 10 mol % based on an amount of said cyanoacetic acid.

14. The process according to claim 1, wherein an amount of said basic catalyst is from 1 to 5 mol % based on an amount of said cyanoacetic acid.

15. The process according to claim 1, wherein said reacting of said crude ester or said purified ester with said ammonia proceeds at a temperature of from 10 to 100° C.

16. The process according to claim 1, wherein said ammonia is used in a stoichiometric amount.

17. The process according to claim 1, wherein said ammonia is in the gaseous state.

* * * * *